(12) United States Patent
Deur-Bert et al.

(10) Patent No.: US 10,947,173 B2
(45) Date of Patent: Mar. 16, 2021

(54) METHOD FOR PURIFYING 1,1,1,2,2-PENTAFLUOROPROPANE

(71) Applicant: Arkema France, Colombes (FR)

(72) Inventors: Dominique Deur-Bert, Charly (FR); Dominique Garrait, Charly (FR); Anne Pigamo, Francheville (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/606,777

(22) PCT Filed: Apr. 20, 2018

(86) PCT No.: PCT/FR2018/050994
§ 371 (c)(1),
(2) Date: Oct. 21, 2019

(87) PCT Pub. No.: WO2018/197787
PCT Pub. Date: Nov. 1, 2018

(65) Prior Publication Data
US 2020/0157026 A1   May 21, 2020

(30) Foreign Application Priority Data
Apr. 28, 2017  (FR) ........................ 1753743

(51) Int. Cl.
*C07C 17/383*  (2006.01)
(52) U.S. Cl.
CPC ................. *C07C 17/383* (2013.01)
(58) Field of Classification Search
CPC ....... C07C 17/383; C07C 17/38; C07C 21/18; C07C 17/206
See application file for complete search history.

(56) References Cited

U.S. PATENT DOCUMENTS

| | | | |
|---|---|---|---|
| 4,902,838 A | 2/1990 | Manzer et al. | |
| 10,207,971 B2 | 2/2019 | Deur-Bert et al. | |
| 2010/0191025 A1 | 7/2010 | Perdrieux | |
| 2014/0012052 A1* | 1/2014 | Pham ................... | C07C 17/383 570/160 |

FOREIGN PATENT DOCUMENTS

| | | |
|---|---|---|
| EP | 939071 A1 | 9/1999 |
| WO | 0181353 A1 | 11/2001 |
| WO | 2007079431 A2 | 7/2007 |
| WO | 2008040969 A2 | 4/2008 |
| WO | 2008054781 A1 | 5/2008 |
| WO | 2008149011 A2 | 12/2008 |
| WO | 2009118628 A1 | 10/2009 |
| WO | 2012067980 A2 | 5/2012 |
| WO | 2013130385 A1 | 9/2013 |
| WO | 2014151448 A2 | 9/2014 |
| WO | 2016059322 A1 | 4/2016 |

OTHER PUBLICATIONS

ISA/EP; International Search Report and Written Opinion for International Patent Application No. PCT/FR2018/050994 dated Jul. 18, 2018, 11 pages.
Bonnet, Philippe, "Liquid-phase HF Fluorination", Multiphase Homogeneous Catalysis, Ed. Wiley-VCH, (2002), pp. 535-542.

\* cited by examiner

*Primary Examiner* — Jafar F Parsa
(74) *Attorney, Agent, or Firm* — NK Patent Law

(57) ABSTRACT

The present invention relates to a process for purifying a stream including 1,1,1,2,2-pentafluoropropane, comprising the steps of i) providing a stream A comprising 1,1,1,2,2-pentafluoropropane and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene; ii) purification, preferably by distillation, of the stream A provided in i) in order to form a first stream A1 comprising 1,1,1,2,2-pentafluoropropane, preferably recovered at the top of the distillation column, and a second stream A2 comprising said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene, preferably recovered at the bottom of the distillation column.

10 Claims, 1 Drawing Sheet

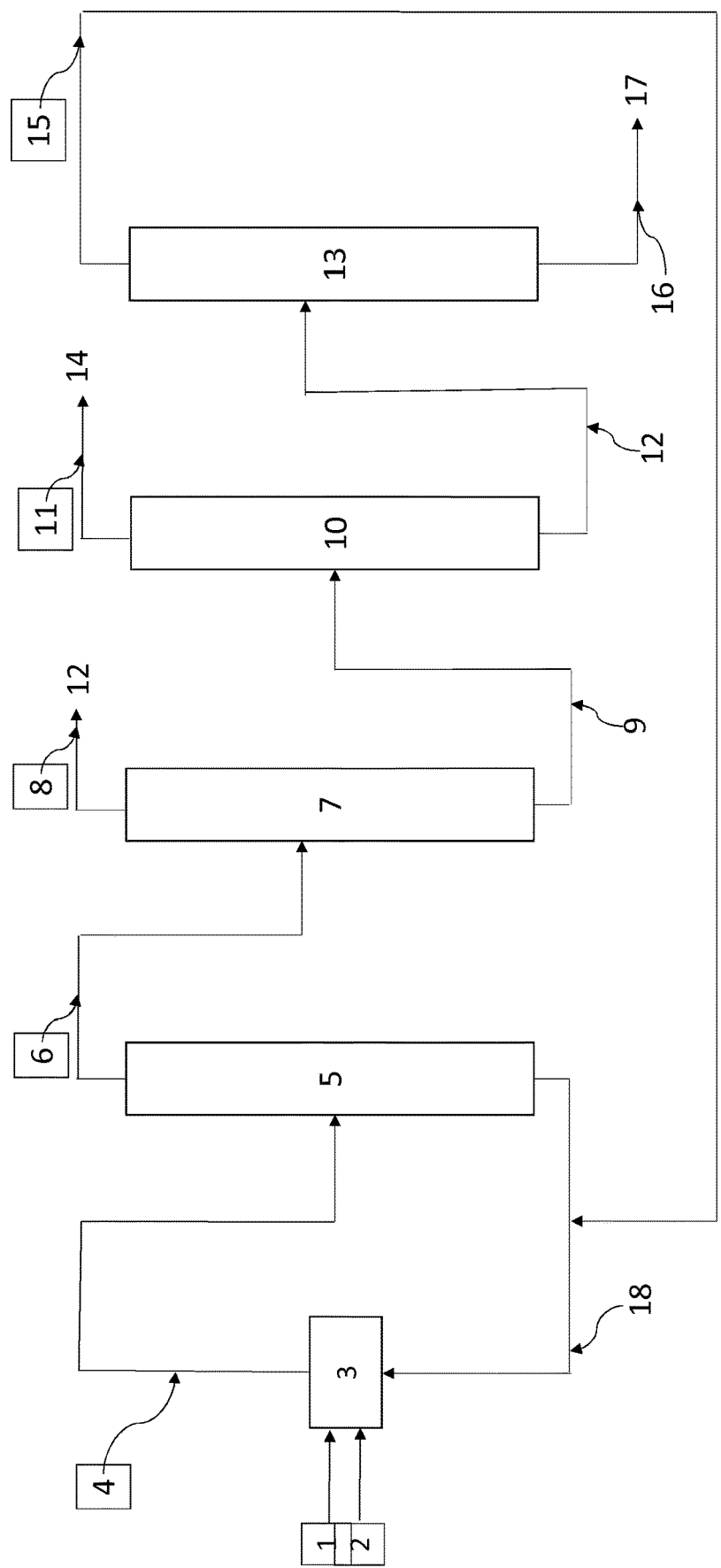

METHOD FOR PURIFYING 1,1,1,2,2-PENTAFLUOROPROPANE

CROSS-REFERENCE TO RELATED APPLICATION

This application is a U.S. National Stage application of International Patent Application No. PCT/FR2018/050994, filed on Apr. 20, 2018, which claims the benefit of French Patent Application No. 1753743, filed on Apr. 28, 2017.

TECHNICAL FIELD

The present invention relates to a process for purifying 1,1,1,2,2-pentafluoropropane. In particular, the present invention relates to the purification of 1,1,1,2,2-pentafluoropropane in the context of a process for producing 2,3,3,3-tetrafluoropropene (HFO-1234yf).

TECHNOLOGICAL BACKGROUND OF THE INVENTION

In a process for gas phase fluorination in the presence of hydrofluoric acid, heavy impurities are generally contained in the excess hydrofluoric acid flow which is recycled in the reaction loop. This flow of HF is obtained by distillation at the bottom of the distillation column, while the desired fluorinated compound (HFO-1234yf) and HCl are recovered at the top. Since a high molar ratio of hydrofluoric acid is used in the reaction loop, this flow of hydrofluoric acid to be recycled mainly contains hydrofluoric acid.

Among the heavy impurities to be removed, those likely to be dehydrochlorinated or dehydrofluorinated to give rise to halogenated propynes are particularly troublesome. These propynes are considered to be extremely unstable and consequently conducive to the formation of oligomers and coke. The recycling and resultant accumulation of these undesirable compounds in the reaction loop contribute in part to the deterioration of the stability (activity and selectivity) of the catalyst. Thus, preventing their accumulation in the reaction loop would therefore make it possible to reduce the rate of coking of the catalyst and thereby improve the stability of the catalyst.

One of the possibilities for eliminating impurities therefrom is to carry out a phase separation by cold settling (temperature <20° C.) on all or a portion of this flow of recycled hydrofluoric acid to obtain an upper phase rich in HF and a rich phase in organics. The phase rich in organics (which therefore contains little HF) can then be treated by distillation to recover the organics of interest (HCFO-1233xf for example) and eliminate the heavy compounds at the bottom. This is especially described in the documents WO2013/130385 and WO2014/151448 which describe a step of settling for obtaining a phase rich in HF and a phase rich in organics, in the context of the step of gas-phase fluorination of the chlorinated compound to give 2-chloro-3,3,3-trifluoropropene (HCFO-1233xf).

However, when the flow of recycled excess hydrofluoric acid comprises too much hydrofluoric acid, the separation of the heavy impurities from the hydrofluoric acid by settling is inefficient, since the flow of HF to be recycled contains a concentration of HF which is greater than or close to that which may be obtained by settling. The organic phase obtained will thus be relatively small relative to the phase rich in HF. Consequently, the purging of undesirable heavy organics may have very poor performance or even be inefficient, despite the means employed. Optionally, a direct purge from this flow of excess recycled HF would be too expensive, since it would involve losing far too much HF in order to eliminate small amounts of organics.

There is therefore a need to provide a process for treating the reaction flows generated in the production of 2,3,3,3-tetrafluoropropene that is more efficient and/or less expensive when it is carried out on an industrial scale.

SUMMARY OF THE INVENTION

The present invention makes it possible to solve the problems described above and observed in the prior art. The present invention makes it possible to carry out a process in which a portion of the heavy compounds are treated with the light impurities rather than with the excess hydrofluoric acid. The compounds are then separated from the lighter impurities. This makes it possible to efficiently eliminate these heavy compounds, to control the contents thereof in the reaction loop to keep them at a low level, and consequently to improve the stability of the catalyst. This process is also more economical and makes it possible to minimize waste. In particular, the applicant identified three heavy impurities, i.e. 2-chloro-1,1,1,3,3-pentafluoropropane (HCFC-235da), 1,2-dichloro-3,3,3-trifluoropropene (HCFO-1223xd), 2-chloro-1,3,3,3-tetrafluoropropene (HCFO-1224xe), when carrying out a process for producing 2,3,3,3-tetrafluoropropene. The nature of these impurities requires carrying out a process for the elimination thereof, while optimizing the overall efficiency of the process and its operational cost.

According to a first aspect, the invention provides a process for purifying a stream including 1,1,1,2,2-pentafluoropropane, comprising the steps of:

i) providing a stream A comprising 1,1,1,2,2-pentafluoropropane and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene;

ii) purification, preferably by distillation, of the stream A provided in i) under conditions effective for forming a first stream A1 comprising 1,1,1,2,2-pentafluoropropane, preferably recovered at the top of the distillation column, and a second stream A2 comprising said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene, preferably recovered at the bottom of the distillation column.

According to a preferred embodiment, the stream A provided in step i) and said second stream A2 of step ii) comprise at least two of the compounds selected from the group consisting of 2-chloro-1,1,1,3,3-pentafluoropropane, 1,2-dichloro-3,3,3-trifluoropropene, 2-chloro-1,3,3,3-tetrafluoropropene, preferably the stream A provided in step i) and said second stream A2 of step ii) comprise 1,1,1,2,2-pentafluoropropane, 2-chloro-1,1,1,3,3-pentafluoropropane, 1,2-dichloro-3,3,3-trifluoropropene, 2-chloro-1,3,3,3-tetrafluoropropene.

According to a preferred embodiment, hydrofluoric acid is also present in said stream A provided in step i).

According to a preferred embodiment, in said first stream A1 obtained in step ii), the 1,1,1,2,2-pentafluoropropane is obtained in the form of an azeotropic or quasi-azeotropic mixture, preferably an azeotropic or quasi-azeotropic mixture comprising 1,1,1,2,2-pentafluoropropane and HF. In particular, said azeotropic or quasi-azeotropic mixture comprising 1,1,1,2,2-pentafluoropropane and HF has a boiling point of between 0 and 60° C. at a pressure of between 1 and 10 bara.

According to a preferred embodiment, the process comprises the addition, to the stream A of step i), of a flow comprising at least 90% of 1,1,1,2,2-pentafluoropropane before carrying out step ii).

According to a preferred embodiment, the stream A provided in step i) also comprises (E/Z)-1,3,3,3-tetrafluoropropene, 2-chloro-3,3,3-trifluoropropene, E-1-chloro-3,3,3-trifluoropropene, Z-1-chloro-3,3,3-trifluoropropene or 1,1,1,3,3-pentafluoropropane.

According to a preferred embodiment, the (E/Z)-1,3,3,3-tetrafluoropropene, 2-chloro-3,3,3-trifluoropropene, E-1-chloro-3,3,3-trifluoropropene or 1,1,1,3,3-pentafluoropropane is (are) recovered in said first stream A1 of step (ii).

Preferably, the stream A2 comprises Z-1-chloro-3,3,3-trifluoropropene.

According to another aspect, the invention provides a process for producing 2,3,3,3-tetrafluoropropene, comprising the steps of:
a) fluorination, in the presence of hydrofluoric acid, of a compound of formula (I) $CH_{(n+2)}(X)_m$—$CH_p(X)_{(n+1)}$—$CX_{(3+p-m)}$ in which X represents independently F or Cl; n, m, p are independently of one another 0 or 1 with (n+m)=0 or 1, (n+p)=0 or 1 and (m–p)=0 or 1, at least one X being Cl, under conditions effective for forming a stream C comprising 2,3,3,3-tetrafluoropropene, 1,1,1,2,2-pentafluoropropane, and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene;
b) purification, preferably by distillation, of the stream C obtained in step a) in order to form a stream C1 comprising 2,3,3,3-tetrafluoropropene and a stream C2 comprising 1,1,1,2,2-pentafluoropropane, and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene,
c) carrying out the process for purifying 1,1,1,2,2-pentafluoropropane according to the present invention using the stream C2 obtained in step b).

According to a preferred embodiment, the stream C obtained in step a) also comprises HF and said stream C obtained in step a) is purified, preferably distilled, prior to step b) in order to form a stream C' comprising 2,3,3,3-tetrafluoropropene, 1,1,1,2,2-pentafluoropropane, and a portion of said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene and a stream C''' comprising HF and a portion of said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene; and step b) is carried out using said stream C'.

According to a preferred embodiment, in the stream C', the total content of said portion of said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene is less than 5% by weight based on the total weight of said stream C'.

According to another aspect, the invention provides a process for treating hydrofluoric acid, comprising the steps of
i') providing a mixture comprising hydrofluoric acid and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene;
ii') distillation of the mixture provided in step i') under conditions effective for forming a stream B1 comprising said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene and a stream B2 comprising hydrofluoric acid.

BRIEF DESCRIPTION OF THE FIGURES

FIG. 1 schematically depicts a particular embodiment of the present invention.

DETAILED DESCRIPTION OF THE INVENTION

According to a first aspect of the present invention, a process for treating hydrofluoric acid is provided. Said process comprises the steps of:
i') providing a mixture comprising hydrofluoric acid and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene;
ii') purification, preferably by distillation, of the mixture provided in step i') under conditions effective for forming a stream B1 comprising said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene and a stream B2 comprising hydrofluoric acid.

Preferably, when step ii') is carried out by distillation the pressure implemented during this step is from 2 to 8 bara, advantageously from 3 to 6 bara, preferably from 3.5 to 5.5 bara; in particular, step ii') is carried out at a pressure of 4 bara.

Preferably, when step ii') is carried out by distillation, the temperature at the top of the distillation column is from −30° C. to 20° C., advantageously from −20° C. to 10° C., preferably from −15° C. to 0° C.

Preferably, when step ii') is carried out by distillation, the temperature at the bottom of the distillation column is from 10° C. to 100° C., advantageously from 20° C. to 90° C., preferably from 30° C. to 80° C., in particular from 40 to 70° C.

According to a preferred embodiment, said mixture of step i') also comprises 2,3,3,3-tetrafluoropropene. Preferably, the 2,3,3,3-tetrafluoropropene is contained in the stream B1 after carrying out step ii').

According to a preferred embodiment, said mixture of step i') also comprises 1,1,1,2,2-pentafluoropropane. Preferably, the 1,1,1,2,2-pentafluoropropane is contained in the stream B1 after carrying out step ii'). When the stream B1 comprises 1,1,1,2,2-pentafluoropropane and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene, said stream B1 corresponds to said stream A according to the present invention and in particular according to the present process for purifying 1,1,1,2,2-pentafluoropropane according to the present invention.

According to a preferred embodiment, said mixture of step i') also comprises (E/Z)-1,3,3,3-tetrafluoropropene and HCl. Preferably, (E/Z)-1,3,3,3-tetrafluoropropene and HCl are contained in the stream B1 after carrying out step ii').

The content of HCl in the stream B1 may be less than 55% by weight, advantageously less than 50% by weight, preferably less than 45% by weight, more preferentially less than 40% by weight, based on the total weight of said stream B1. The content of (E/Z)-1,3,3,3-tetrafluoropropene in the stream B1 may be less than 15% by weight, advantageously less than 10% by weight, preferably less than 5% by weight, based on the total weight of said stream B1.

Preferably, said mixture of step i') also comprises 2,3,3,3-tetrafluoropropene and this is preferentially recovered in the stream B1. The content of 2,3,3,3-tetrafluoropropene in the stream B1 may be less than 50% by weight, advantageously less than 45% by weight, preferably less than 40% by weight, more preferentially less than 35% by weight, in particular less than 30% by weight, more particularly less than 25% by weight, based on the total weight of said stream B1.

Preferably, said mixture of step i') also comprises 1,1,1,2,2-pentafluoropropane and this is preferentially recovered in the stream B1. The content of 1,1,1,2,2-pentafluoropropane in the stream B1 may be less than 50% by weight, advantageously less than 45% by weight, preferably less than 40% by weight, more preferentially less than 35% by weight, in particular less than 30% by weight, based on the total weight of said stream B1.

Preferably, said mixture of step i') also comprises 2-chloro-3,3,3-trifluoropropene. In this case, at least a portion of the 2-chloro-3,3,3-trifluoropropene is contained in the stream B1 after carrying out step ii'). The content of 2-chloro-3,3,3-trifluoropropene in said stream B1 is less than 20% by weight, based on the total weight of said stream B1, advantageously less than 18% by weight, preferably less than 16% by weight, more preferentially less than 14% by weight, in particular less than 12% by weight, more particularly less than 10% by weight, based on the total weight of said stream B1.

The total content of said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene in the stream B1 is less than 5% by weight, based on the total weight of the stream B1, advantageously less than 4% by weight, preferably less than 3% by weight, more preferentially less than 2% by weight, in particular less than 1% by weight, based on the total weight of the stream B1.

Preferably, the content of 2-chloro-1,1,1,3,3-pentafluoropropane in said stream B1 is less than 4% by weight, based on the total weight of said stream B1, advantageously less than 3% by weight, preferably less than 2% by weight, more preferentially less than 1% by weight, in particular less than 0.8% by weight, more particularly less than 0.5% by weight, based on the total weight of said stream B1.

Preferably, the content of 1,2-dichloro-3,3,3-trifluoropropene in said stream B1 is less than 4% by weight, based on the total weight of said stream B1, advantageously less than 3% by weight, preferably less than 2% by weight, more preferentially less than 1% by weight, in particular less than 0.8% by weight, more particularly less than 0.5% by weight, based on the total weight of said stream B1.

Preferably, the content of 2-chloro-1,3,3,3-tetrafluoropropene in said stream B1 is less than 4% by weight, based on the total weight of said stream B1, advantageously less than 3% by weight, preferably less than 2% by weight, more preferentially less than 1% by weight, in particular less than 0.8% by weight, more particularly less than 0.5% by weight, based on the total weight of said stream B1.

A portion of the 2-chloro-3,3,3-trifluoropropene may also be contained in the stream B2 after carrying out step ii').

According to a preferred embodiment, said mixture of step i') also comprises (E/Z)-1-chloro-3,3,3-trifluoropropene and 1,1,1,3,3-pentafluoropropane. Preferably, the (E/Z)-1-chloro-3,3,3-trifluoropropene and 1,1,1,3,3-pentafluoropropane are contained in the stream B2 after carrying out step ii'). Nevertheless, a portion of the (E/Z)-1-chloro-3,3,3-trifluoropropene may be contained in the stream B1 after carrying out step ii'). In particular, a portion of the E-1-chloro-3,3,3-trifluoro-1-propene (HCFO-1233zdE) may be contained in said stream B1. The content of E-1-chloro-3,3,3-trifluoro-1-propene (HCFO-1233zdE) in the stream B1 may be less than 2% by weight, based on the total weight of the stream B1, advantageously less than 1% by weight, preferably less than 0.5% by weight, based on the total weight of the stream B1.

Preferably, the content of hydrofluoric acid is greater than 80 mol % in said stream B2 obtained in step ii'), advantageously greater than 82 mol %, preferably greater than 84 mol %, more preferentially greater than 86 mol %, in particular greater than 88 mol %, more particularly greater than 90 mol %, in said stream B2 obtained in step ii'). However, a portion of the hydrofluoric acid may be present in the stream B1. The content of hydrofluoric acid in the stream B1 is less than 15% by weight, based on the total weight of the stream B1, advantageously less than 14% by weight, preferably less than 13% by weight, more preferentially less than 10% by weight, based on the total weight of the stream B1.

The stream B1 obtained in step ii') can be distilled in order to remove any hydrochloric acid present. This distillation may be carried out under conditions such that the temperature at the top of the distillation column may be between −10° C. and −70° C., more preferentially between −15° C. and −65° C., in particular between −20° C. and −60° C., more particularly between −25° C. and −60° C., favorably between −30° C. and −60° C.; and the pressure at the top of the distillation column may be between 2 and 20 bara, advantageously between 3 and 15 bara, preferably between 4 and 10 bara. More particularly, the stream B1 may be brought to a temperature of less than 100° C. before being distilled. Thus, the stream B1 may be at a temperature of less than 95° C., less than 90° C., less than 85° C., less than 80° C., less than 75° C., less than 70° C., less than 65° C., less than 60° C., less than 55° C., less than 50° C., less than 45° C., less than 40° C., less than 35° C., less than 30° C., less than 25° C., less than 20° C., less than 15° C., less than 10° C., less than 5° C. or less than 0° C. before being distilled.

According to another aspect, the invention provides a process for purifying a stream comprising 1,1,1,2,2-pentafluoropropane. Preferably, the stream comprising the 1,1,1,2,2-pentafluoropropane is a stream A comprising 1,1,1,2,2-pentafluoropropane and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene. Said stream A may correspond to the stream B1 as described above and obtained by carrying out the process for treating hydrofluoric acid according to the present invention. Preferably, said stream A may correspond to the stream B1 when the latter does not contain hydrochloric acid. The stream B1 can be distilled to remove hydrochloric acid as described above.

Said process for purifying a stream comprising 1,1,1,2,2-pentafluoropropane comprises the steps of:

i) providing a stream A comprising 1,1,1,2,2-pentafluoropropane and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene;

ii) purification, preferably by distillation, of the stream A provided in i) under conditions effective for forming a first stream A1 comprising 1,1,1,2,2-pentafluoropropane, preferably recovered at the top of the distillation column, and a second stream A2 comprising said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene, preferably recovered at the bottom of the distillation column.

According to a preferred embodiment, the stream A provided in step i) and said second stream A2 of step ii) comprise at least two of the compounds selected from the group consisting of 2-chloro-1,1,1,3,3-pentafluoropropane, 1,2-dichloro-3,3,3-trifluoropropene, 2-chloro-1,3,3,3-tetrafluoropropene, preferably the stream A provided in step i) and said second stream A2 of step ii) comprise 1,1,1,2,2-pentafluoropropane, 2-chloro-1,1,1,3,3-pentafluoropropane, 1,2-dichloro-3,3,3-trifluoropropene and 2-chloro-1,3,3,3-tetrafluoropropene.

Preferably, the content of 1,1,1,2,2-pentafluoropropane in said stream A is less than 75% by weight, based on the total weight of said stream A, advantageously less than 74% by weight, preferably less than 73% by weight, more preferentially less than 72% by weight, in particular less than 71% by weight, more particularly less than 70% by weight, based on the total weight of said stream A.

The content of said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene in the stream A is less than 5% by weight, based on the total weight of the stream A, advantageously less than 4% by weight, preferably less than 3% by weight, more preferentially less than 2% by weight, in particular less than 1% by weight based on the total weight of the stream A.

According to a preferred embodiment, hydrofluoric acid is also present in said stream A provided in step i).

The content of hydrofluoric acid in the stream A is less than 15% by weight, based on the total weight of the stream A, advantageously less than 14% by weight, preferably less than 13% by weight, more preferentially less than 12% by weight, based on the total weight of the stream A.

According to a preferred embodiment, in said first stream A1 obtained in step ii), the 1,1,1,2,2-pentafluoropropane is obtained in the form of an azeotropic or quasi-azeotropic mixture, preferably an azeotropic or quasi-azeotropic mixture comprising 1,1,1,2,2-pentafluoropropane and HF.

Preferably, the content of 1,1,1,2,2-pentafluoropropane in the stream A1 is greater than 50% by weight, advantageously greater than 55% by weight, preferably greater than 60% by weight, based on the total weight of the stream A1. In particular, the content of 1,1,1,2,2-pentafluoropropane in the stream A1 is 60 to 70% by weight of 1,1,1,2,2-pentafluoropropane.

Said first stream A1 may optionally comprise small amounts of one of the compounds selected from the group consisting of 2-chloro-1,1,1,3,3-pentafluoropropane, 1,2-dichloro-3,3,3-trifluoropropene and 2-chloro-1,3,3,3-tetrafluoropropene. Preferably, the total content of 2-chloro-1,1,1,3,3-pentafluoropropane, 1,2-dichloro-3,3,3-trifluoropropene, 2-chloro-1,3,3,3-tetrafluoropropene in said first stream A1 obtained in step ii) is less than 5% by weight, based on the total weight of said first stream A1, advantageously less than 4% by weight, preferably less than 3% by weight, more preferentially less than 2% by weight, in particular less than 1% by weight, more particularly less than 0.5% by weight, based on the total weight of said first stream A1 obtained in step ii). Thus, even if the first stream A1 obtained in step ii) comprises heavy impurities such as 2-chloro-1,1,1,3,3-pentafluoropropane, 1,2-dichloro-3,3,3-trifluoropropene, 2-chloro-1,3,3,3-tetrafluoropropene, the content, expressed in moles, thereof in said first stream A1 is less than the content, expressed in moles, thereof in said stream A.

Preferably, the content of 2-chloro-1,1,1,3,3-pentafluoropropane in said stream A1 is less than 4% by weight, based on the total weight of said stream A1, advantageously less than 3% by weight, preferably less than 2% by weight, more preferentially less than 1% by weight, in particular less than 0.8% by weight, more particularly less than 0.5% by weight, based on the total weight of said stream A1.

Preferably, the content of 1,2-dichloro-3,3,3-trifluoropropene in said stream A1 is less than 4% by weight, based on the total weight of said stream A1, advantageously less than 3% by weight, preferably less than 2% by weight, more preferentially less than 1% by weight, in particular less than 0.8% by weight, more particularly less than 0.5% by weight, based on the total weight of said stream A1.

Preferably, the content of 2-chloro-1,3,3,3-tetrafluoropropene in said stream A1 is less than 4% by weight, based on the total weight of said stream A1, advantageously less than 3% by weight, preferably less than 2% by weight, more preferentially less than 1% by weight, in particular less than 0.8% by weight, more particularly less than 0.5% by weight, based on the total weight of said stream A1.

Preferably, the process comprises the addition, to the stream A of step i), of a flow comprising at least 70% of 1,1,1,2,2-pentafluoropropane before carrying out step ii), advantageously at least 75% of 1,1,1,2,2-pentafluoropropane, preferably at least 80% of 1,1,1,2,2-pentafluoropropane, more preferentially at least 85% of 1,1,1,2,2-pentafluoropropane, in particular at least 90% of 1,1,1,2,2-pentafluoropropane, more particularly at least 95% of 1,1,1,2,2-pentafluoropropane by weight based on the total weight of said flow.

According to a preferred embodiment, the stream A provided in step i) also comprises (E/Z)-1,3,3,3-tetrafluoropropene, 2-chloro-3,3,3-trifluoropropene, E-1-chloro-3,3,3-trifluoropropene, Z-1-chloro-3,3,3-trifluoropropene or 1,1,1,3,3-pentafluoropropane.

According to a preferred embodiment, the (E/Z)-1,3,3,3-tetrafluoropropene, 2-chloro-3,3,3-trifluoropropene, E-1-chloro-3,3,3-trifluoropropene or 1,1,1,3,3-pentafluoropropane is (are) recovered in said first stream A1 of step (ii). Preferably, the Z-1-chloro-3,3,3-trifluoropropene is recovered in said stream A2 of step ii).

Preferably, the content of (E/Z)-1,3,3,3-tetrafluoropropene in said first stream A1 of step ii) is less than 10% by weight, based on the total weight of said first stream A1 of step ii), advantageously less than 9% by weight, preferably less than 8% by weight, more preferentially less than 7% by weight, in particular less than 6% by weight, more particularly less than 5% by weight, based on the total weight of said first stream A1 of step ii).

Preferably, the content of 2-chloro-3,3,3-trifluoropropene in said first stream A1 of step ii) is less than 20% by weight, based on the total weight of said first stream A1 of step ii), advantageously less than 19% by weight, preferably less than 18% by weight, more preferentially less than 17% by weight, in particular less than 16% by weight, more particularly less than 15% by weight, based on the total weight of said first stream A1 of step ii).

Preferably, the content of E-1-chloro-3,3,3-trifluoropropene in said first stream A1 of step ii) is less than 5% by weight, based on the total weight of said first stream A1 of step ii), advantageously less than 4% by weight, preferably less than 3% by weight, more preferentially less than 2% by weight, in particular less than 1% by weight, more particularly less than 0.5% by weight, based on the total weight of said first stream A1 of step ii).

Preferably, the content of 1,1,1,3,3-pentafluoropropane in said first stream A1 of step ii) is less than 5% by weight, based on the total weight of said first stream A1 of step ii), advantageously less than 4% by weight, preferably less than 3% by weight, more preferentially less than 2% by weight, in particular less than 1% by weight, more particularly less than 0.5% by weight, based on the total weight of said first stream A1 of step ii).

Preferably, the content of hydrofluoric acid in said first stream A1 of step ii) is less than 15% by weight, based on the total weight of said first stream A1 of step ii), advantageously less than 14% by weight, preferably less than 13% by weight, more preferentially less than 12% by weight, in particular less than 11% by weight, more particularly less than 10% by weight, based on the total weight of said first stream A1 of step ii).

In particular, said first stream A1 obtained in step ii) comprises an azeotropic or quasi-azeotropic mixture comprising HF, 1,1,1,2,2-pentafluoropropane and optionally (E/Z)-1,3,3,3-tetrafluoropropene, 2-chloro-3,3,3-trifluoropropene, E-1-chloro-3,3,3-trifluoropropene or 1,1,1,3,3-pentafluoropropane, said azeotropic or quasi-azeotropic mixture having a boiling point of between 0 and 60° C. at a pressure of between 1 and 10 bara.

Preferably, step ii) is carried out by distillation, the temperature at the top of the distillation column is between 0 and 60° C. In particular, the pressure is between 1 and 10 bara.

Said first stream A1 obtained in step ii) thus purified can be recycled in order to be used in a process for producing 2,3,3,3-tetrafluoropropene. In particular, said first stream A1 obtained in step ii) can feed a reactor in which a fluorination reaction of 2-chloro-3,3,3-trifluoropropene is carried out. More particularly, said first stream A1 obtained in step ii) can be mixed with a flow comprising hydrofluoric acid before feeding a reactor in which a fluorination reaction of 2-chloro-3,3,3-trifluoropropene is carried out.

According to another aspect of the present invention, a process for producing 2,3,3,3-tetrafluoropropene is provided. Said process comprises the steps of:

a) fluorination, in the presence of hydrofluoric acid, of a compound of formula (I) $CH_{(n+2)}(X)_m$—$CH_p(X)_{(n+1)}$—$CX_{(3+p-m)}$ in which X represents independently F or Cl; n, m, p are independently of one another 0 or 1 with (n+m)=0 or 1, (n+p)=0 or 1 and (m-p)=0 or 1, at least one X being Cl, under conditions effective for forming a stream C comprising 2,3,3,3-tetrafluoropropene, 1,1,1,2,2-pentafluoropropane, and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene;

b) purification, preferably by distillation, of the stream C obtained in step a) in order to form a stream C1 comprising 2,3,3,3-tetrafluoropropene and a stream C2 comprising 1,1,1,2,2-pentafluoropropane, and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene;

c) carrying out the process for purifying 1,1,1,2,2-pentafluoropropane using the stream C2 obtained in step b).

Preferably, the compound of formula (I) is selected from the group consisting of 1,1,1,2,3-pentachloropropane, 1,1,2,3-tetrachloropropane, 2,3,3,3-tetrachloropropene, 2-chloro-3,3,3-trifluoropropene, 1,2-dichloro-3,3,3-trifluoropropane and 2-chloro-1,1,1,2-tetrafluoropropane, or a mixture thereof. In particular, the compound of formula (I) is 1,1,1,2,3-pentachloropropane, 2-chloro-3,3,3-trifluoropropene, 1,2-dichloro-3,3,3-trifluoropropane or 1,1,2,3-tetrachloropropene.

Preferably, step a) of the present process is carried out in the gas phase. Step a) of the present process may be carried out in the presence or absence of a catalyst. When it is carried out in the gas phase and in the presence of a catalyst, step a) can be carried out in the presence of a catalyst based on a metal comprising a transition metal oxide or a derivative or a halide or an oxyhalide of such a metal. Mention may be made, for example, of $FeCl_3$, chromium oxyfluoride, chromium oxides (optionally subjected to fluorination treatments), chromium fluorides and their mixtures. Other possible catalysts are catalysts supported on carbon, antimony-based catalysts or aluminum-based catalysts (for example $AlF_3$ and $Al_2O_3$, aluminum oxyfluoride and aluminum fluoride). Use may be made in general of a chromium oxyfluoride, an aluminum fluoride or oxyfluoride, or a supported or nonsupported catalyst containing a metal such as Cr, Ni, Fe, Zn, Ti, V, Zr, Mo, Ge, Sn, Pb, Mg or Sb. Reference may be made, in this regard, to the document WO 2007/079431 (on p. 7, l. 1-5 and 28-32), to the document EP 939 071 (section [0022]), to the document WO 2008/054781 (on p. 9, l. 22-p. 10, l. 34) and to the document WO 2008/040969 (claim 1), to which documents reference is expressly made. The catalyst is more particularly preferably based on chromium and it is more particularly a mixed catalyst comprising chromium. According to one embodiment, for any one of the reaction steps use is made of a mixed catalyst comprising chromium and nickel. The Cr/Ni molar ratio (on the basis of the metal element) is generally from 0.5 to 5, for example from 0.7 to 2, for example approximately 1. The catalyst can contain from 0.5% to 20% by weight of nickel. The metal may be present in metallic form or in the form of a derivative, for example an oxide, halide or oxyhalide. These derivatives are preferably obtained by activation of the catalytic metal. The support is preferably formed with aluminum, for example alumina, activated alumina or aluminum derivatives, such as aluminum halides and aluminum oxyhalides, for example described in the document U.S. Pat. No. 4,902,838, or obtained by the activation process described above. The catalyst can comprise chromium and nickel in an activated or nonactivated form, on a support which has or has not been subjected to an activation. Reference may be made to the document WO 2009/118628 (in particular on p. 4, l. 30-p. 7, l. 16), to which reference is expressly made here. Another preferred embodiment is based on a mixed catalyst containing chromium and at least one cocatalyst chosen from Co, Mn, Mg and Zn salts, preferably Zn salts. Said cocatalyst is preferably present in a content of 1% to 10% by weight, based on the weight of the catalyst. Before its use, the catalyst is preferably subjected to an activation with air, oxygen or chlorine and/or with HF. For example, the catalyst is preferably subjected to an activation with air or oxygen and HF at a temperature of 100 to 500° C., preferably of 250 to 500° C. and more particularly of 300 to 400° C. The duration of activation is preferably from 1 to 200 h and more particularly from 1 to 50 h. This activation can be followed by a final fluorination activation step in the presence of an oxidizing agent, HF and organic compounds. The HF/organic compounds molar ratio is preferably from 2 to 40 and the oxidizing agent/organic compounds molar ratio is preferably from 0.04 to 25. The temperature of the final activation is preferably from 300 to 400° C. and its duration is preferably from 6 to 100 h.

In the gas phase, step a) of the present process may be carried out at a temperature of 200 to 450° C., advantageously 250 to 400° C., preferably 280 to 380° C. Step a) of the present process may be carried out with a contact time of 3 to 100 s, advantageously 4 to 75 s, preferably 5 to 50 s. Step a) of the present process may be carried out with a molar ratio of HF/compound of formula (I) of 3:1 to 150:1, advantageously 4:1 to 125:1, preferably 5:1 to 100:1. The process, preferably step a), can be carried out in the presence of a polymerization inhibitor, preferably selected from the group consisting of p-methoxyphenol, t-amylphenol, limonene, d,1-limonene, quinones, hydroquinones, epoxides, amines and mixtures thereof. Step a) of the present process can be carried out in the presence of oxygen or chlorine, advantageously 0.005 to 15 mol %, preferably 0.5 to 10 mol % of oxygen or chlorine per mole of compound of formula (I). Step a) is carried out at a pressure of 1 to 20 bara, preferably 2 to 15 bara, in particular 3 to 10 bara.

Preferably, step a) of the present process is carried out in the gas phase in the presence of a catalyst and a compound of formula (I) selected from the group consisting of 1,1,1,2,3-pentachloropropane, 2-chloro-3,3,3-trifluoropropene, 1,2-dichloro-3,3,3-trifluoropropane or 1,1,2,3-tetrachloropropene.

Alternatively, step a) of the present process may be carried out in the liquid phase in the presence of a catalyst. The catalyst may be a Lewis acid, a catalyst containing a metal halide, in particular a halide of antimony, tin, tantalum, titanium, a transition metal such as molybdenum, niobium, iron, cesium, transition metal oxides, halides of group IVb metals, halides of group Vb metals, chromium fluoride, fluorinated chromium oxides or a mixture thereof. For example, the catalyst may be $SbCl_5$, $SbCl_3$, $TiCl_4$, $SnCl_4$, $TaCl_5$, $NbCl_5$, $TiCl_4$, $FeCl_3$, $MoCl_6$, CsCl, and the corresponding fluorinated compounds. The catalyst may contain an ionic liquid, as described for example in applications WO2008/149011 (in particular from page 4, line 1 to page 6, line 15, incorporated by reference) and WO01/81353, and also the reference "liquid-phase HF Fluorination", Multiphase Homogeneous Catalysis, Ed. Wiley-VCH, (2002), 535. In the liquid phase, step a) may be carried out at a temperature of between 30 and 200° C., advantageously between 40° C. and 170° C., preferably between 50 and 150° C. Preferably, the molar ratio of HF/compound of formula (I) may be from 0.5:1 to 50:1, advantageously from 3:1 to 20:1 and preferably from 5:1 to 15:1.

Preferably, the stream C obtained in step a) also comprises HF and said stream C obtained in step a) is purified, preferably distilled, prior to step b), step denoted a1). The stream C may correspond to the stream B1 described above when it comprises 2,3,3,3-tetrafluoropropene, 1,1,1,2,2-pentafluoropropane, HF and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene. Thus, the purification, preferably the distillation, enables the formation of a stream C' comprising 2,3,3,3-tetrafluoropropene, 1,1,1,2,2-pentafluoropropane, and a portion of said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene and a stream C'' comprising HF and a portion of said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene.

Preferably, when step a1) is carried out by distillation, the pressure implemented during this step is from 2 to 8 bara, advantageously from 3 to 6 bara, preferably from 3.5 to 5.5 bara; in particular, step a1) is carried out at a pressure of 4 bara.

Preferably, when step a1) is carried out by distillation, the temperature at the top of the distillation column is from −30° C. to 20° C., advantageously from −20° C. to 10° C., preferably from −15° C. to 0° C.

Preferably, when step a1) is carried out by distillation, the temperature at the bottom of the distillation column is from 10° C. to 100° C., advantageously from 20° C. to 90° C., preferably from 30° C. to 80° C., in particular from 40 to 70° C.

Thus, the stream C' can be treated according to step b) of the present process for producing 2,3,3,3-tetrafluoropropene.

Preferably, when the stream C comprises HCl, the latter will preferably be contained in the stream C'. In particular, when the stream C' comprises HCl, said stream C' is subjected to a distillation step a2) subsequently to the step a1) and prior to the step b) in order to form a stream C''', preferably at the top of the distillation column, comprising HCl and a stream C'''', preferably at the bottom of the distillation column, comprising 2,3,3,3-tetrafluoropropene, 1,1,1,2,2-pentafluoropropane, and a portion of said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene. Preferably, the temperature at the top of the distillation column used in step a2) may be between −10° C. and −70° C., more preferentially between −15° C. and −65° C., in particular between −20° C. and −60° C., more particularly between −25° C. and −60° C., favorably between −30° C. and −60° C.

According to a preferred embodiment, the pressure at the top of the distillation column used in step a2) may be between 2 and 20 bara, advantageously between 3 and 15 bara, preferably between 4 and 10 bara. More particularly, the stream C' may be brought to a temperature of less than 100° C. before being distilled. Thus, the stream C' may be at a temperature of less than 95° C., less than 90° C., less than 85° C., less than 80° C., less than 75° C., less than 70° C., less than 65° C., less than 60° C., less than 55° C., less than 50° C., less than 45° C., less than 40° C., less than 35° C., less than 30° C., less than 25° C., less than 20° C., less than 15° C., less than 10° C., less than 5° C. or less than 0° C. before being distilled.

In particular, the stream C'''' can be treated according to step b) of the present process for producing 2,3,3,3-tetrafluoropropene.

Thus, the present process for producing 2,3,3,3-tetrafluoropropene comprises the steps of:
a) fluorination, in the presence of hydrofluoric acid, of a compound of formula (I) $CH_{(n+2)}(X)_m-CH_p(X)_{(n+1)}-CX_{(3+p-m)}$ in which X represents independently F or Cl; n, m, p are independently of one another 0 or 1 with (n+m)=0 or 1, (n+p)=0 or 1 and (m−p)=0 or 1, at least one X being Cl, under conditions effective for forming a stream C comprising 2,3,3,3-tetrafluoropropene, 1,1,1,2,2-pentafluoropropane, and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene and optionally HF and optionally HCl;

a1) optional purification, preferably distillation, of the stream C in order to form a stream C' comprising 2,3,3,3-tetrafluoropropene, 1,1,1,2,2-pentafluoropropane, and a portion of said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene and optionally HCl; and a stream C'' comprising HF and a portion of said at least one of the compounds selected from the group consisting of 2-chloro-1,1,3,3-pentafluoropropane, 1,2-dichloro-3,3,3-trifluoropropene, 2-chloro-1,3,3,3-tetrafluoropropene;

a2) optional purification, preferably distillation, of the stream C' obtained in step a1) in order to form a stream C''', preferably at the top of the distillation column, comprising HCl and a stream C'''', preferably at the bottom of the distillation column, comprising 2,3,3,3-tetrafluoropropene, 1,1,1,2,2-pentafluoropropane, and said one portion of said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene;

b) purification, preferably by distillation, of the stream C obtained in step a) or of the stream C' obtained in step a1) or of the stream C'''' obtained in step a2) in order to form a stream C1 comprising 2,3,3,3-tetrafluoropropene and a stream C2 comprising 1,1,1,2,2-pentafluoropropane, and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene;

c) carrying out the process for purifying 1,1,1,2,2-pentafluoropropane according to the present invention using the stream C2 obtained in step b) and purification, preferably by distillation, of the stream C2 in order to form a first stream C3 comprising 1,1,1,2,2-pentafluoropropane, preferably recovered at the top of the distillation column, and a second stream C4 comprising said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene, preferably recovered at the bottom of the distillation column. Preferably, said streams C3 and C4 correspond respectively to the streams A1 and A2 described in relation to the process for purifying 1,1,1,2,2-pentafluoropropane according to the present invention.

According to a preferred embodiment, the temperature at the top of the distillation column in step b) is between 0° C. and 50° C. Preferably, the pressure at the top of the distillation column in step b) is between 3 and 12 bara.

Preferably, in the stream C' and/or the stream C'''', the content of said portion of said at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene is less than 10% by weight based on the total weight of said stream C' or C'''', advantageously less than 9% by weight based on the total weight of said stream C' or C'''', preferably less than 8% by weight based on the total weight of said stream C' or C'''', more preferentially less than 7% by weight based on the total weight of said stream C' or C'''', in particular less than 6% by weight based on the total weight of said stream C' or C'''', more particularly less than 5% by weight based on the total weight of said stream C' or C'''', favorably less than 4% by weight based on the total weight of said stream C' or C'''', more favorably less than 3% by weight based on the total weight of said stream C' or C''''.

The stream C1 may comprise at least 40% by weight of 2,3,3,3-tetrafluoropropene, advantageously at least 45% by weight, preferably at least 50% by weight, more preferentially at least 55% by weight, in particular at least 60% by weight, more particularly at least 65% by weight, favorably at least 70% by weight based on the total weight of the stream C1.

The stream C1 may optionally comprise small amounts of 1,1,1,2,2-pentafluoropropane. Preferably, the content of 1,1,1,2,2-pentafluoropropane in said stream C1 is less than 40% by weight, based on the total weight of said stream C1, advantageously less than 35% by weight, preferably less than 30% by weight, more preferentially less than 25% by weight, in particular less than 22% by weight, more particularly less than 20% by weight, based on the total weight of said stream C1.

The stream C1 may optionally comprise small amounts of hydrofluoric acid. Preferably, the content of hydrofluoric acid in said stream C1 is less than 20% by weight, based on the total weight of said stream C1, advantageously less than 18% by weight, preferably less than 16% by weight, more preferentially less than 14% by weight, in particular less than 12% by weight, more particularly less than 10% by weight, based on the total weight of said stream C1.

As mentioned above, the stream C2 comprises 1,1,1,2,2-pentafluoropropane and at least one of the compounds selected from the group consisting of 2-chloro-1,1,1,3,3-pentafluoropropane, 1,2-dichloro-3,3,3-trifluoropropene, 2-chloro-1,3,3,3-tetrafluoropropene.

Preferably, the content of 1,1,1,2,2-pentafluoropropane in the stream C2 is less than 75% by weight, based on the total weight of said stream C2, advantageously less than 74% by weight, preferably less than 73% by weight, more preferentially less than 72% by weight, in particular less than 71% by weight, more particularly less than 70% by weight, based on the total weight of said stream C2.

Preferably, the total content of 2-chloro-1,1,1,3,3-pentafluoropropane, 1,2-dichloro-3,3,3-trifluoropropene, 2-chloro-1,3,3,3-tetrafluoropropene in said first stream C2 is less than 5% by weight, based on the total weight of said first stream C2, advantageously less than 4% by weight, preferably less than 3% by weight, more preferentially less than 2% by weight, in particular less than 1% by weight, more particularly less than 0.5% by weight, based on the total weight of said first stream C2.

Preferably, the content of 2-chloro-1,1,1,3,3-pentafluoropropane in said stream C2 is less than 4% by weight, based on the total weight of said stream C2, advantageously less than 3% by weight, preferably less than 2% by weight, more preferentially less than 1% by weight, in particular less than 0.8% by weight, more particularly less than 0.5% by weight, based on the total weight of said stream C2.

Preferably, the content of 1,2-dichloro-3,3,3-trifluoropropene in said stream C2 is less than 4% by weight, based on the total weight of said stream C2, advantageously less than 3% by weight, preferably less than 2% by weight, more preferentially less than 1% by weight, in particular less than 0.8% by weight, more particularly less than 0.5% by weight, based on the total weight of said stream C2.

Preferably, the content of 2-chloro-1,3,3,3-tetrafluoropropene in said stream C2 is less than 4% by weight, based on the total weight of said stream C2, advantageously less than 3% by weight, preferably less than 2% by weight, more preferentially less than 1% by weight, in particular less than 0.8% by weight, more particularly less than 0.5% by weight, based on the total weight of said stream C2.

As described above in relation to the process for purifying 1,1,1,2,2-pentafluoropropane, hydrofluoric acid may be present in the stream C, C', C"", C2, C3 and C4. Preferably, the content of hydrofluoric acid in the stream C2 is less than 15% by weight, based on the total weight of the stream C2, advantageously less than 14% by weight, preferably less than 13% by weight, more preferentially less than 12% by weight, based on the total weight of the stream C2. According to a preferred embodiment, said first stream C3 comprises an azeotropic or quasi-azeotropic mixture, preferably an azeotropic or quasi-azeotropic mixture comprising 1,1,1,2,2-pentafluoropropane and HF.

Preferably, the content of 1,1,1,2,2-pentafluoropropane in the stream C3 is greater than 50% by weight, advantageously greater than 55% by weight, preferably greater than 60% by weight, based on the total weight of the stream C3. In particular, the content of 1,1,1,2,2-pentafluoropropane in the stream C3 is 60 to 70% by weight of 1,1,1,2,2-pentafluoropropane.

Said stream C3 may optionally comprise small amounts of one of the compounds selected from the group consisting of 2-chloro-1,1,1,3,3-pentafluoropropane, 1,2-dichloro-3,3,3-trifluoropropene and 2-chloro-1,3,3,3-tetrafluoropropene. Preferably, the total content of 2-chloro-1,1,1,3,3-pentafluoropropane, 1,2-dichloro-3,3,3-trifluoropropene, 2-chloro-1,3,3,3-tetrafluoropropene in said first stream C3 is less than 5% by weight, based on the total weight of said stream C3, advantageously less than 4% by weight, preferably less than 3% by weight, more preferentially less than 2% by weight, in particular less than 1% by weight, more particularly less than 0.5% by weight, based on the total weight of said stream C3.

Preferably, the content of 2-chloro-1,1,1,3,3-pentafluoropropane in said stream C3 is less than 4% by weight, based on the total weight of said stream C3, advantageously less than 3% by weight, preferably less than 2% by weight, more preferentially less than 1% by weight, in particular less than 0.8% by weight, more particularly less than 0.5% by weight, based on the total weight of said stream C3.

Preferably, the content of 1,2-dichloro-3,3,3-trifluoropropene in said stream C3 is less than 4% by weight, based on the total weight of said stream C3, advantageously less than 3% by weight, preferably less than 2% by weight, more preferentially less than 1% by weight, in particular less than 0.8% by weight, more particularly less than 0.5% by weight, based on the total weight of said stream C3.

Preferably, the content of 2-chloro-1,3,3,3-tetrafluoropropene in said stream C3 is less than 4% by weight, based on the total weight of said stream C3, advantageously less than 3% by weight, preferably less than 2% by weight, more preferentially less than 1% by weight, in particular less than 0.8% by weight, more particularly less than 0.5% by weight, based on the total weight of said stream C3.

Preferably, the process comprises the addition, to the stream C2 of step i), of a flow comprising at least 70% of 1,1,1,2,2-pentafluoropropane before carrying out step ii), advantageously at least 75% of 1,1,1,2,2-pentafluoropropane, preferably at least 80% of 1,1,1,2,2-pentafluoropropane, more preferentially at least 85% of 1,1,1,2,2-pentafluoropropane, in particular at least 90% of 1,1,1,2,2-pentafluoropropane, more particularly at least 95% of 1,1,1,2,2-pentafluoropropane by weight based on the total weight of said flow.

According to a preferred embodiment, the stream C, C', C"", C2 and C3 also comprise (E/Z)-1,3,3,3-tetrafluoropropene, 2-chloro-3,3,3-trifluoropropene, E-1-chloro-3,3,3-trifluoropropene, or 1,1,1,3,3-pentafluoropropane.

According to a preferred embodiment, the (E/Z)-1,3,3,3-tetrafluoropropene, 2-chloro-3,3,3-trifluoropropene, E-1-chloro-3,3,3-trifluoropropene or 1,1,1,3,3-pentafluoropropane is (are) recovered in said stream C3.

Preferably, the content of (E/Z)-1,3,3,3-tetrafluoropropene in said stream C3 is less than 10% by weight, based on the total weight of said stream C3, advantageously less than 9% by weight, preferably less than 8% by weight, more preferentially less than 7% by weight, in particular less than 6% by weight, more particularly less than 5% by weight, based on the total weight of said stream C3.

Preferably, the content of 2-chloro-3,3,3-trifluoropropene in said stream C3 is less than 20% by weight, based on the total weight of said stream C3, advantageously less than 19% by weight, preferably less than 18% by weight, more preferentially less than 17% by weight, in particular less than 16% by weight, more particularly less than 15% by weight, based on the total weight of said stream C3.

Preferably, the content of E-1-chloro-3,3,3-trifluoropropene in said stream C3 is less than 5% by weight, based on the total weight of said stream C3, advantageously less than 4% by weight, preferably less than 3% by weight, more preferentially less than 2% by weight, in particular less than 1% by weight, more particularly less than 0.5% by weight, based on the total weight of said stream C3.

Preferably, the content of 1,1,1,3,3-pentafluoropropane in said stream C3 is less than 5% by weight, based on the total weight of said stream C3, advantageously less than 4% by weight, preferably less than 3% by weight, more preferentially less than 2% by weight, in particular less than 1% by weight, more particularly less than 0.5% by weight, based on the total weight of said stream C3.

Preferably, the content of hydrofluoric acid in said stream C3 is less than 15% by weight, based on the total weight of said stream C3, advantageously less than 14% by weight, preferably less than 13% by weight, more preferentially less than 12% by weight, in particular less than 11% by weight, more particularly less than 10% by weight, based on the total weight of said stream C3.

In particular, said stream C3 comprises an azeotropic or quasi-azeotropic mixture comprising HF, 1,1,1,2,2-pentafluoropropane and optionally (E/Z)-1,3,3,3-tetrafluoropropene, 2-chloro-3,3,3-trifluoropropene, E-1-chloro-3,3,3-trifluoropropene or 1,1,1,3,3-pentafluoropropane, said mixture having a boiling point of between 0 and 60° C. at a pressure of between 1 and 10 bara. Preferably, step c) is carried out by distillation, the temperature at the top of the distillation column is between 0 and 60° C. In particular, the pressure is between 1 and 10 bara.

Said stream C3 thus purified can be recycled in step a) of the present process for producing 2,3,3,3-tetrafluoropropene.

According to a preferred embodiment, the stream C, C', C"", C2 and C4 comprise Z-1-chloro-3,3,3-trifluoropropene.

Preferably, at least 95% of the cis-1-chloro-3,3,3-trifluoro-1-propene (HCFO-1233zdZ) contained in the stream C2 is recovered in the stream C4; advantageously, at least 96%, preferably at least 97%, more preferentially at least 98%, in particular at least 99%, more particularly at least 99.5%, of the cis-1-chloro-3,3,3-trifluoro-1-propene (HCFO-1233zdZ) contained in the stream C2 is recovered in the stream C4.

Preferably, at least 80% of the 2-chloro-1,1,1,3,3-pentafluoropropane (HCFC-235da) contained in the stream C2 is recovered in the stream C4; advantageously, at least 85%, preferably at least 90%, more preferentially at least 93%, in particular at least 94%, more particularly at least 95%, of the 2-chloro-1,1,1,3,3-pentafluoropropane (HCFC-235da) contained in the stream C2 is recovered in the stream C4. In particular, from 90% to 98% of the 2-chloro-1,1,1,3,3-pentafluoropropane (HCFC-235da) contained in the stream C2 is recovered in the stream C4.

Preferably, at least 80% of the 1,2-dichloro-3,3,3-trifluoropropene (HCFO-1223xd) contained in the stream C2 is recovered in the stream C4; advantageously, at least 85%, preferably at least 90%, more preferentially at least 93%, in particular at least 94%, more particularly at least 95%, of the 1,2-dichloro-3,3,3-trifluoropropene (HCFO-1223xd) contained in the stream C2 is recovered in the stream C4. In particular, from 90% to 98% of the 1,2-dichloro-3,3,3-trifluoropropene (HCFO-1223xd) contained in the stream C2 is recovered in the stream C4.

Preferably, at least 80% of the 2-chloro-1,3,3,3-tetrafluoropropene (HCFO-1224xe) contained in the stream C2 is recovered in the stream C4; advantageously, at least 85%, preferably at least 90%, more preferentially at least 93%, in particular at least 94%, more particularly at least 95%, of the 2-chloro-1,3,3,3-tetrafluoropropene (HCFO-1224xe) contained in the stream C2 is recovered in the stream C4. In particular, from 90% to 98% of the 2-chloro-1,3,3,3-tetrafluoropropene (HCFO-1224xe) contained in the stream C2 is recovered in the stream C4.

Preferably, said stream C4 comprises from 1% to 25% by weight of 2-chloro-1,3,3,3-tetrafluoropropene (HCFO-1224xe), advantageously from 5% to 20% by weight, preferably from 7% to 18% by weight, in particular from 10% to 15% by weight, of 2-chloro-1,3,3,3-tetrafluoropropene (HCFO-1224xe), based on the total weight of said stream C4.

Preferably, said stream C4 comprises from 40% to 85% by weight of 1,2-dichloro-3,3,3-trifluoropropene (HCFO-1223xd), advantageously from 45% to 80% by weight, preferably from 50% to 75% by weight, in particular from 55% to 70% by weight, of 1,2-dichloro-3,3,3-trifluoropropene (HCFO-1223xd), based on the total weight of said stream C4.

Preferably, said stream C4 comprises from 1% to 25% by weight of 2-chloro-1,1,1,3,3-pentafluoropropane (HCFC-235da), advantageously from 5% to 20% by weight, preferably from 7% to 18% by weight, in particular from 10% to 15% by weight, of 2-chloro-1,1,1,3,3-pentafluoropropane (HCFC-235da), based on the total weight of said stream C4.

Preferably, said stream C4 comprises from 0.05% to 10% by weight of cis-1-chloro-3,3,3-trifluoro-1-propene (HCFO-1233zdZ), advantageously from 0.1% to 8% by weight, preferably from 0.5% to 7% by weight, in particular from 1% to 5% by weight, of cis-1-chloro-3,3,3-trifluoro-1-propene (HCFO-1233zdZ), based on the total weight of said stream C4.

Thus, said stream C4 may comprise from 1% to 5% by weight of cis-1-chloro-3,3,3-trifluoro-1-propene (HCFO-1233zdZ), from 10% to 15% by weight of 2-chloro-1,1,1,3,3-pentafluoropropane (HCFC-235da), from 55% to 70% by weight of 1,2-dichloro-3,3,3-trifluoropropene (HCFO-1223xd), from 10% to 15% by weight of 2-chloro-1,3,3,3-tetrafluoropropene (HCFO-1224xe).

Preferably, the stream C4 comprises less than 2% by weight of hydrofluoric acid, based on the total weight of the stream C4, advantageously less than 1% by weight, preferably less than 0.5% by weight, in particular less than 0.1% by weight, of hydrofluoric acid, based on the total weight of the stream C4.

FIG. 1 schematically depicts a process for producing 2,3,3,3-tetrafluoropropene including the process for purifying 1,1,1,2,2-pentafluoropropane and the process for treating hydrofluoric acid according to the present invention. Hydrofluoric acid 1 is brought into contact with 1,1,1,2,3-pentachloropropane (HCC-240db) 2 in one or more reactors 3. The bringing into contact is carried out under conditions effective for forming a mixture C comprising 2,3,3,3-tetrafluoropropene, 1,1,1,2,2-pentafluoropropane, HCl, HF, 2-chloro-1,1,1,3,3-pentafluoropropane, 1,2-dichloro-3,3,3-trifluoropropene and 2-chloro-1,3,3,3-tetrafluoropropene. Said mixture is recovered at the outlet of reactor 3 and conveyed to a distillation column 5 via the pipe 4. The mixture C is distilled so as to form a stream C' comprising 2,3,3,3-tetrafluoropropene, 1,1,1,2,2-pentafluoropropane, HCl, 2-chloro-1,1,1,3,3-pentafluoropropane, 1,2-dichloro-3,3,3-trifluoropropene and 2-chloro-1,3,3,3-tetrafluoropropene and a stream C" comprising HF, 2-chloro-1,1,1,3,3-pentafluoropropane, 1,2-dichloro-3,3,3-trifluoropropene and 2-chloro-1,3,3,3-tetrafluoropropene. The stream C', recovered at the top of distillation column 5, is conveyed via the pipe 6 to the distillation column 7. The stream C", recovered at the bottom of the distillation column 5, is conveyed via the pipe 18 to the reactor 3 to be recycled in the fluorination reaction of 1,1,1,2,3-pentachloropropane after optional purification. The stream C' is distilled in 7 to form, at the top of the distillation column, a stream C''' comprising HCl which may optionally be conveyed via the pipe 8 to a purification device 12. A stream C'''' is recovered at the bottom of the distillation column and is conveyed via the pipe 9 to the distillation column 10. The stream C'''' comprises 2,3,3,3-tetrafluoro-1-propene, 1,1,1,2,2-pentafluoropropane, 2-chloro-1,1,1,3,3-pentafluoropropane, 1,2-dichloro-3,3,3-trifluoropropene and 2-chloro-1,3,3,3-tetrafluoropropene. The distillation column 10 enables the separation between on the one hand 2,3,3,3-tetrafluoropropene (stream C1) and on the other hand 1,1,1,2,2-pentafluoropropane, 2-chloro-1,1,1,3,3-pentafluoropropane, 1,2-dichloro-3,3,3-trifluoropropene and 2-chloro-1,3,3,3-tetrafluoropropene (stream C2). The stream C1 recovered at the top of the distillation column is conveyed to the purification device 14 via the pipe 11. The stream C2 is conveyed to the distillation column 13 via the pipe 12. The distillation column 13 enables the separation between on the one hand 1,1,1,2,2-pentafluoropropane (stream C3) and on the other hand 2-chloro-1,1,1,3,3-pentafluoropropane, 1,2-dichloro-3,3,3-trifluoropropene and 2-chloro-1,3,3,3-tetrafluoropropene (stream C4). The stream C3 is recycled to the reactor 3 via the pipes 15 and 18. The stream C4 is recovered at the bottom of the distillation column and for example conveyed to an incinerator 17 via the pipe 16. The stream C3 comprises small amounts of 2-chloro-1,1,1,3,3-pentafluoropropane, 1,2-dichloro-3,3,3-trifluoropropene and 2-chloro-1,3,3,3-tetrafluoropropene as explained in the present application. The present invention makes it possible to purify the flow of 1,1,1,2,2-pentafluoropropane of heavy compounds and thereby improve the overall process for producing 2,3,3,3-tetrafluoropropene by avoiding the accumulation of compounds such as 2-chloro-1,1,1,3,3-pentafluoropropane, 1,2-dichloro-3,3,3-trifluoropropene and 2-chloro-1,3,3,3-tetrafluoropropene in the reaction loop. This is further achieved by optimizing the recovery of unreacted hydrofluoric acid.

EXAMPLE

Example 1

A stream comprising 87% of 1,1,1,2,2-pentafluoropropane, 10% of HF, 1% of 2-chloro-1,1,1,3,3-pentafluoropropane, 0.8% of 1,2-dichloro-3,3,3-trifluoropropene and 0.5% of 2-chloro-1,3,3,3-tetrafluoropropene by weight is distilled under conditions such that the temperature at the top of the distillation column is from 0 to 60° C. and the pressure is from 1 to 10 bara. The stream obtained at the top of the distillation column comprises 5% by weight of HF, 0.1% of 2-chloro-1,1,1,3,3-pentafluoropropane, 0.2% of 1,2-dichloro-3,3,3-trifluoropropene and 0.05% of 2-chloro-1,3,3,3-tetrafluoropropene by weight, the remainder being 1,1,1,2,2-pentafluoropropane.

Example 2

A stream comprising 76.6% of 1,1,1,2,2-pentafluoropropane, 8% of HF, 0.7% of 2-chloro-1,1,1,3,3-pentafluoropropane, 0.6% of 1,2-dichloro-3,3,3-trifluoropropene, 0.5% of 2-chloro-1,3,3,3-tetrafluoropropene, 3% of 1,3,3,3-tetrafluoropropene, 10% of 2-chloro-3,3,3-trifluoropropene, 0.4% of E-1-chloro-3,3,3-trifluoropropene, 0.2% of 1,1,1,3,3-pentafluoropropane by weight is distilled under conditions such that the temperature at the top of the distillation column is from 0 to 60° C. and the pressure is from 1 to 10 bara. The stream obtained at the top of the distillation column comprises 5% by weight of HF, 0.15% of 2-chloro-1,1,1,3,3-pentafluoropropane, 0.1% of 1,2-dichloro-3,3,3-trifluoropropene, 0.03% of 2-chloro-1,3,3,3-tetrafluoropropene, 3% of 1,3,3,3-tetrafluoropropene, 10% of 2-chloro-3,3,3-trifluoropropene, 0.3% of E-1-chloro-3,3,3-trifluoropropene, 0.2% of 1,1,1,3,3-pentafluoropropane by weight, the remainder being 1,1,1,2,2-pentafluoropropane.

The invention claimed is:

1. A process for purifying a stream including 1,1,1,2,2-pentafluoropropane, comprising the steps of:
   i) providing a stream A comprising at least 50% 1,1,1,2,2-pentafluoropropane and at least one of the compounds selected from the group consisting of 2-chloro-1,1,1,3,3-pentafluoropropane, 1,2-dichloro-3,3,3-trifluoropropene, and 2-chloro-1,3,3,3-tetrafluoropropene; and
   ii) purifying stream A provided in i) under conditions effective for forming a first stream A1 comprising 1,1,1,2,2-pentafluoropropane and a second stream A2 comprising said at least one of the compounds selected from the group consisting of 2-chloro-1,1,1,3,3-pentafluoropropane, 1,2-dichloro-3,3,3-trifluoropropene, and 2-chloro-1,3,3,3-tetrafluoropropene.

2. The process as claimed in claim 1, wherein stream A provided in step i) and second stream A2 of step ii) comprise at least two of the compounds selected from the group consisting of 2-chloro-1,1,1,3,3-pentafluoropropane, 1,2-dichloro-3,3,3-trifluoropropene, and 2-chloro-1,3,3,3-tetrafluoropropene.

3. The process as claimed in claim 1, wherein stream A further comprises hydrofluoric acid.

4. The process as claimed in claim 1, wherein in first stream A1 obtained in step ii), the 1,1,1,2,2-pentafluoropropane is obtained in the form of an azeotropic or quasi-azeotropic mixture.

5. The process as claimed in claim 1, further comprising adding a flow comprising at least 90% of 1,1,1,2,2-pentafluoropropane to the stream A of step i) before carrying out step ii).

6. The process as claimed in claim 1, wherein stream A provided in step i) further comprises (E/Z)-1,3,3,3-tetrafluoropropene, 2-chloro-3,3,3-trifluoropropene, E-1-chloro-3,3,3-trifluoropropene, Z-1-chloro-3,3,3-trifluoropropene or 1,1,1,3,3-pentafluoropropane.

7. The process as claimed in claim 6, wherein the (E/Z)-1,3,3,3-tetrafluoropropene, 2-chloro-3,3,3-trifluoropropene, E-1-chloro-3,3,3-trifluoropropene or 1,1,1,3,3-pentafluoropropane is (are) recovered in said first stream A1 of step (ii).

8. The process of claim 1, wherein stream A is purified by distillation.

9. The process of claim 2, wherein stream A provided in step i) and second stream A2 of step ii) comprise 1,1,1,2,2-pentafluoropropane, 2-chloro-1,1,1,3,3-pentafluoropropane, 1,2-dichloro-3,3,3-trifluoropropene, and 2-chloro-1,3,3,3-tetrafluoropropene.

10. The process of claim 4, wherein the azeotropic or quasi-azeotropic mixture comprises 1,1,1,2,2-pentafluoropropane and HF.

* * * * *